United States Patent [19]

Rey et al.

[11] B 3,993,742

[45] Nov. 23, 1976

[54] METHOD FOR THE DETECTION OF FATTY SUBSTANCES ON SURFACES

[75] Inventors: Hans-Georg Rey; Walter Rittersdorf, both of Mannheim-Woldhof; Ernst-Werner Busch, Lampertheim, all of Germany

[73] Assignee: Boehringer Mannheim G.m.b.H., Mannheim, Germany

[22] Filed: Dec. 19, 1973

[21] Appl. No.: 426,424

[44] Published under the second Trial Voluntary Protest Program on February 3, 1976 as document No. B 426,424.

Related U.S. Application Data

[62] Division of Ser. No. 219,566, Jan. 20, 1972, abandoned.

[30] Foreign Application Priority Data

Feb. 11, 1971 Germany............................ 2106408

[52] U.S. Cl..................................... 424/9; 424/14; 424/16; 424/32; 424/35

[51] Int. Cl.$^2$................. A61K 29/00; G01N 13/00; G01N 21/04

[58] Field of Search ............... 424/9, 14, 16, 32, 35; 117/36.7

[56] References Cited

UNITED STATES PATENTS

| 2,519,660 | 8/1950 | James | 117/36.7 |
| 2,710,263 | 6/1955 | Clark | 117/36.7 |
| 2,854,350 | 9/1958 | Phillpotts | 117/36.7 |
| 2,939,802 | 6/1960 | Werle | 117/36.7 |
| 2,957,791 | 10/1960 | Bechtold | 117/36.7 |
| 3,431,131 | 3/1969 | Hartman | 117/36.7 |

FOREIGN PATENTS OR APPLICATIONS

| 849,011 | 11/1939 | France | 424/27 |
| 1,171,869 | 11/1969 | United Kingdom | 424/9 |

*Primary Examiner*—V. D. Turner
*Assistant Examiner*—A. P. Fagelson
*Attorney, Agent, or Firm*—Burgess, Dinklage & Sprung

[57] ABSTRACT

A diagnostic composition comprising a base material and a light colored coating material thereon, wherein the base material has a dark color on its coated side, and the coating material is a finely dispersed microporous plastic applied in a thickness sufficient for the complete masking of the color of the base material, is outstandingly effective in detecting fat or fat-like substances on surfaces by merely contacting the composition with the surface.

9 Claims, No Drawings

METHOD FOR THE DETECTION OF FATTY SUBSTANCES ON SURFACES

This is a division of application Ser. No. 219,566, filed Jan. 20, 1972, now abandoned.

The present invention relates to diagnostic compositions and to methods for the detection of fat or fat-like substances on surfaces using such compositions, especially for the detection of fat or fat-like substances on human skin, i.e. of the skin oil of the human body.

In connection with the diagnosis of skin diseases, e.g., seborrhea, it is very important to be able to simply and rapidly detect the oil content of the skin. For this purpose a series of methods have been developed, but they are all time-consuming, difficult and more or less inaccurate.

The most accurate method to date is the so-called osmium test. In this test filter paper is pressed against the skin area to be tested, for a number of minutes; after 24 hours the paper is developed for two minutes with osmium-VIII oxide vapors. The skin oil picked up by the filter paper reduces the osmium-VIII oxide to lower oxides or to metallic osmium. The dark-colored areas are approximately proportional in degree of blackening to the amount of skin oil absorbed, and they can be evaluated photometrically. Aside from the fact that osmium oxide is very toxic, the performance of this test is time-consuming and can be performed only in the laboratory.

It is also possible to dye the skin fat absorbed by the filter paper with Sudan black, but this method gives even more inaccurate results than development with osmium-VIII oxide.

Another method of detection consists in pressing a filter paper impregnated with anthracene against the skin area for 30 minutes and then studying it under ultraviolet light. The skin oil absorbed by the filter paper extinguishes the fluorescence of the anthracene as seen in ultraviolet light and this results in the formation of dark specks. This method of detection is extremely difficult, requires the availability of an ultraviolet lamp, and is not very sensitive. Since anthracene is furthermore considered as a potentially carcinogenic substance, it can, at any rate, no longer be used for a skin test.

As it is apparent from the state of the art described above, there were, prior to this invention, no available means for the detection of oil on the skin sufficiently fast, simple and accurate that it could be used as a quick testing method for general use by medical auxiliary personnel, cosmeticians or lay people.

The present invention provides a novel detection composition and method of detection which, without the need for laboratory instruments, is capable of giving precise, reliable and quick information on the state of the human skin and can thus be used as a quick test even by lay people. The instant method makes it possible especially for cosmeticians and women of cosmetic skill to determine at any time the state of the human skin and to govern accordingly the application of cosmetic preparations such as soaps, skin creams and skin lotions. It is known, for instance, that oily skin requires entirely different care from normal or dry skin.

It has now surprisingly been found that a film, or foil, provided with a light-colored, preferably white, face coating is outstandingly suited to serve as a diagnostic means for the detection of fat and fat-like substances on surfaces, especially on the human skin. In this invention, the face coating, applied onto the film, consists of a finely dispersed plastic material having microporous interstices, and is applied in sufficient thickness to completely mask the color of the base (film) material. The film is, on its coated side, a dark, contrasting color, preferably black.

Papers of sufficient strength, colored black on one side, are normally used as the film. The face coating is prepared quite simply by dissolving plastics, especially cellulose esters or cellulose ethers, in a polar solvent containing water, coating the paper with this solution, and carefully drying it, preferably in moist air. In this procedure, a "white bloom" is produced by the face coating, i.e., as the face coating dries it forms a white coating in which the plastic is distributed in finely divided form and contains microporous voids.

Papers of the above-described kind have been used successfully in the prior art as copy paper and record paper (cf. U.S. Pat. Nos. 2,519,660 and 2,939,802), but it has never before been recognized that these papers are irreversibly blackened by fats and oils and react so sensitively to fat and fat-like substances that, when applied to the human skin, they immediately produce a precise and surprisingly clear image of the distribution of the sebum. Amazingly, body sweat does not interfere with this test, because it produces a blackening which soon completely vanishes, while the coloring produced by sebum remains.

In addition to the above-described visibilization of skin oil, any surface provided with a thin layer of fat or oil can be made visible in accordance with the invention. For example, it is possible in the practice of crime detection to produce very clear fingerprints from slightly oiled fingers, thereby eliminating the common soiling of the fingertips with ink. The impressions obtained can be preserved indefinitely.

Furthermore, the present invention makes possible the preparation of prints of the soles of the feet in orthopedics. All the patient need do is to place the foot, which has previously been treated with an oily cream, for example, on the paper; when the foot is pressed down, a very sharp imprint is then obtained of the sole of the foot.

Needless to say, the process of the invention is not restricted to surfaces of the body, but also can be applied to the study of and to the preparation of impressions of other surfaces, such as wood grain patterns, or printing plates.

The following plastics are examples of those which can be used in making the face coating: cellulose butyrate, cellulose oleate, cellulose stearate, cellulose phthalate, cellulose naphthenate, cellulose laurate, cellulose acetobutyrate, cellulose acctomaleate, cellulose acetonitrate, ethyl cellulose, benzyl cellulose, nitrocellulose, ethyl cellulose nitrate, benzyl cellulose acetate, ethyl cellulose acetate, glycol cellulose acetate. In addition to cellulose derivatives, other polymers can be used, such as polymethylmethacrylate or polystyrene, for example.

The solvents used to dissolve the plastic material are preferably mixtures which have not only a certain miscibility with water but also sufficient solvent characteristics in relation to the plastic. The characteristics of the mixture can be modified in the desired manner by the addition of polar solvents. Examples of the solvents are: benzene, acetone, ether, dichlorethylene, carbon tetrachloride, toluene, dioxane, acetic ester, methyl ethyl ketone, ethanol, n-propanol, butyl acetate, methyl isobutyl ketone, and xylene.

Cross-linking agents and/or plasticizers, such as dibutyl phthalate, tris-(ethylhexyl)-phosphate or bis-(methoxy-ethyl)-phthalate, can also be added to modify the face coating.

Generally, the weight ratio of solvent to water is from about 50:1 to 1:1, preferably from 20:1 to 3:1; and the weight ratio of the solvent/water mixture to plastic material is from 50:1 to 1:1, preferably from 25:1 to 10:1.

The application of the face coating to the film is done in a thickness of approximately 5 to 50 microns. Depending on the intensity of the "blooming" effect, a complete covering of the contrasting color of the base material is achieved in this manner. The drying is performed by means of moist air (50–70% relative humidity), although air of low moisture content can also be used. In the former case, after-drying is necessary.

The film consists preferably of paper of adequate strength and pliability but plastic film or metal foils can, of course, also be used.

The invention is illustrated in the following examples:

EXAMPLE 1

Smooth black paper was coated with a layer approximately 10 microns thick of a solution of the following composition:

| | |
|---|---|
| ethyl cellulose | 10.0 g |
| acetone | 110.0 g |
| tris-(ethylhexyl)-phosphate | 1.5 g |
| water | 20.0 g |

The applied coating was dried in the air, whereupon a gray-white surface forms which turns black upon contact with fat and fat-like substances.

EXAMPLE 2

Polyvinyl chloride film blackened on one side was coated as in Example 1 with a solution of the following composition:

| | |
|---|---|
| acetyl cellulose | 5 g |
| acetone | 80 g |
| bis-(methoxyethyl)-phthalate | 0.75 g |
| water | 25 g |

The whittish coating turned black upon contact with fat and fat-like substances.

EXAMPLE 3

As in Example 1, black paper was coated with a solution of the following composition:

| | |
|---|---|
| ethyl cellulose | 7.0 g |
| acetone | 25.0 g |
| methanol | 118.0 g |
| water | 7.0 g |

The sensitivity of the test paper to skin oils complies with all requirements.

EXAMPLE 4

The test films obtained in accordance with Examples 1 to 3 were cut into pieces 5 cm square, laid with the coating against the skin, preferably against the side of the nostrils and the forehead, and gently pressed against it for 1 second. An irregular pattern of black dots was obtained on the white coating, corresponding to the sebaceous glands of the skin. On the basis of the amount, size, distribution and degree of blackening it is possible to judge the degree of oiliness of the skin. If the skin was moist with perspiration a more or less uniform blackening formed, but it faded completely after 10 to 20 seconds and left only the pattern corresponding to the oiliness of the skin.

It will be understood that the specification and examples are illustrative but not limitative of the present invention and that other embodiments within the spirit and scope of the invention will suggest themselves to those skilled in the art.

What is claimed is:

1. Method for detecting fat or fat-like substances on a surface, which consists essentially of contacting the surface with the plastic material coated surface of a diagnostic means, thereby immediately producing a clear image of the distribution of the fat or fat-like substances on said surface, said means comprising a film, foil, or paper having a dark base color and a face coating in a thickness sufficient to mask the color of the base, said face coating comprising a finely dispersed plastic material having microporous interstices and having a white bloom, said plastic material being selected from the group consisting of cellulose butyrate, cellulose oleate, cellulose stearate, cellulose phthalate, cellulose naphthenate, cellulose laurate, cellulose acetobutyrate, cellulose acetomaleate, cellulose acetonitrate, ethyl cellulose, acetyl cellulose, benzyl cellulose, nitrocellulose, ethyl cellulose nitrate, benzyl cellulose acetate, ethyl cellulose acetate, glycol cellulose acetate, polymethacrylate and polystyrene.

2. The method of claim 1, wherein said surface is human skin.

3. The method of claim 1 wherein the dark base color is black on the coated side.

4. The method of claim 1 wherein said plastic material is ethyl cellulose or acetyl cellulose.

5. The method of claim 1 wherein the thickness of the face coating is 5 to 50 microns.

6. The method of claim 1 wherein said diagnostic means comprises a coated film or foil.

7. The method of claim 6 wherein said film or foil is paper.

8. The method of claim 6 wherein said film or foil is a plastic film.

9. The method of claim 6 wherein said film or foil is a metal foil.

* * * * *